United States Patent
Graninger et al.

(10) Patent No.: US 8,940,517 B2
(45) Date of Patent: Jan. 27, 2015

(54) METHODS FOR ISOLATING AND QUANTIFYING ANTIGEN FROM VACCINES

(75) Inventors: Michael Graninger, Vienna (AT); Martin Kaliwoda, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/450,026

(22) Filed: Apr. 18, 2012

(65) Prior Publication Data

US 2012/0270255 A1 Oct. 25, 2012

Related U.S. Application Data

(60) Provisional application No. 61/477,835, filed on Apr. 21, 2011.

(51) Int. Cl.

| | |
|---|---|
| *C12N 7/00* | (2006.01) |
| *C12N 7/01* | (2006.01) |
| *C12N 7/02* | (2006.01) |
| *C12N 7/04* | (2006.01) |
| *C12N 7/06* | (2006.01) |
| *A61K 39/145* | (2006.01) |
| *C07K 4/02* | (2006.01) |
| *C07K 1/14* | (2006.01) |
| *C07K 14/005* | (2006.01) |

(52) U.S. Cl.
CPC .............. *C07K 14/005* (2013.01); *C12N 7/00* (2013.01); *C12N 2760/16051* (2013.01); *C12N 2760/16151* (2013.01)
USPC ........ 435/235.1; 435/236; 435/238; 435/239; 424/206.1; 424/184.1; 530/396

(58) Field of Classification Search
CPC ............ C07K 1/14; C07K 1/145; C07K 1/16; C07K 1/20; C12N 7/00; C12N 2760/16051; C12N 2760/16151
See application file for complete search history.

(56) References Cited

U.S. PATENT DOCUMENTS

| 7,687,611 B2 | 3/2010 | Kapteyn et al. | |
|---|---|---|---|
| 2005/0118594 A1* | 6/2005 | Chawla et al. | 435/6 |

FOREIGN PATENT DOCUMENTS

EP 1725581 B1 11/2006

OTHER PUBLICATIONS

Influenza reagent, Influenza anti-A/Bangkok/1/79 (H3N2)(X73) HA serum, National Institute for Biological Standards and Control, 2008, retrieved on Apr. 22, 2013. Retrieved from the Internet <URL: nibsc.ac.uk/documents/ifu/80-525.pdf>.*

Beilstein et al. Selenoprotein W of rat muscle binds glutathione and an unknown small molecular weight moiety. Journal of Inorganic Biochemistry, 1996, vol. 61, p. 117-124.*
2-Mercaptoethanol, Fisher Scientific, Material Safety Data Sheet, retrieved on Sep. 13, 2013. Retrieved from Internet <URL: fishersci.ca/viewmsds.do?catNo=O3446I100>.*
TCEP Reducing Resin, G Biosciences, retrieved on Sep. 19, 2013. Retrieved from Internet <URL: gbiosciences.com/PDF/Protocol/TCEP_Reducing_Resin.pdf>.*
Yan et al. High-temperature ultrafast liquid chromatography. Analytical Chemistry, 2000, vol. 72, p. 1253-1262.*
DTT, Dithiothreitol, 2010 AG Scientific, Inc., retrieved on Sep. 19, 2013. Retrieved from Internet <URL:agscientific.com/dtt-1.html>.*
Garcia-Canas et al., Approach to the profiling and characterization of influenca vaccine constituents by the combined use of size-exclusion chromatography, gel electrophoresis and mass spectrometry. *Biologicals* 38: 294-302 (2010).
Garcia-Canas et al., Rapid and selective characterization of influenza virus constituents in monovalent and multivalent preparations using non-porous reversed-phase high performance liquid chromatography columns. *J. Chromat. A.* 1123: 225-32 (2006).
Garcia-Canas et al., Selective and quantitative detection of influenza virus proteins in commercial vaccines using two-dimensional high-performance liquid chromatography and fluorescence detection. *Anal. Chem.* 79(8): 3164-72 (2007).
Genbank Accession No. ABU50586.1, hemagglutinin [Influenza A virus (A/Solomon Islands/3/2006(H1N1))], dated May 1, 2008.
Genbank Accession No. ACQ55359.1, hemagglutinin [Influenza A virus (A/California/07/2009(H1N1))], dated Jun. 1, 2009.
Kapteyn et al., Haemagglutinin quantification and identification of influenza A&B strains propagated in PER.C6® cells: A novel RP-HPLC method. *Vaccine* 24: 3137-44 (2006).
Kapteyn et al., HPLC-based quantification of haemagglutinin in the production of egg- and MDCK cell-derived influenza virus seasonal and pandemis vaccines. *Vaccine* 27: 1468-77 (2009).
Lorbetskie et al., Optimization and qualification of a quantitative reversed-phase HPLC method for hemagglutinin in influenca preparations and its comparative evaluation with biochemical assays. *Vaccine* 29: 3377-89 (2011).
Phelan et al., Gradient optimization principles in reversed-phase high-performance liquid chromatography and the separation of influenza virus components. *J. Chromatogr.* 266: 55-66 (1983).
Behrendt et al., The human receptor for urokinase plasminogen activator NH2-terminal amino acid sequence and glycosylation variants. *J. Biol. Chem.* 265(11): 6543-60 (1990).

(Continued)

*Primary Examiner* — Louise Humphrey

(74) *Attorney, Agent, or Firm* — Marshall, Gerstein & Borun LLP

(57) ABSTRACT

The disclosure relates to the development of improved methods for quantifying antigen in a vaccine composition in the absence of available antigen standards. More specifically, the disclosure provides fast and robust methods of separating antigens from vaccine compositions, comprising the steps of solubilizing antigen without detergent and without alkylation, using acidification to prevent antigen subtypes from binding again, isolating antigen subtypes with chromatography, and quantifying the eluted antigen with amino acid analysis. The methods of the disclosure are applicable for use with a variety of antigens, thereby providing an improved method in the art of vaccine manufacturing to date.

29 Claims, No Drawings

(56) References Cited

OTHER PUBLICATIONS

Crankshaw et al., Modification of Cysteine. Current Protocols in Protein Science Editorial Board, Chapter 15, Unit 15.1, 2001.
Li et al., Application of deglycosylation and electrophoresis to the quantification of influenza viral hemagglutinins facilitating the production of 2009 pandemic influenza (H1N1) vaccines at multiple manufacturing sites in China. *Biologicals* 38(2): 284-9 (2010).
International Search Report and Written Opinion of the International Searching Authority issued in connection with International Application No. PCT/US2012/034054, European Searching Authority, mailed Jul. 13, 2012.

* cited by examiner

METHODS FOR ISOLATING AND QUANTIFYING ANTIGEN FROM VACCINES

RELATED APPLICATIONS

This application claims benefit of U.S. Provisional Patent Application Ser. No. 61/477,835, filed Apr. 21, 2011, which is incorporated herein by reference in its entirety.

FIELD

The disclosure generally relates to the field of vaccines and methods for isolating and measuring antigen content in a vaccine without a known standard.

BACKGROUND

Influenza viruses are generally divided into three types: A, B, and C, based on antigenic differences between their nucleoprotein antigens and matrix protein antigens. Influenza viruses are further divided into subtypes depending on the antigenic nature of the two major viral surface glycoproteins, hemagglutinin (HA) and neuraminidase (NA). Both HA and NA carry antigenic epitopes. Antibodies that are raised against HA and NA are associated with resistance to infection and/or illness in humans and animals. The efficacy of a vaccination against Influenza is largely determined by the amount of immunogenic HA in a vaccine. Thus, the major antigenic determinant of Influenza A and B virus is HA and the efficacy of a vaccination against Influenza is largely determined by the amount of immunogenic HA, i.e., antigen content, in a vaccine.

To date, antigen content is measured with international standards supplied by World Health Organization Collaborating Centers (hereinafter "WHO"), which are used for the determination of the antigen value, e.g., HA content of vaccines. Often, however, vaccines are prepared by vaccine manufacturers when standards are not available, for example, when there are antigenic differences (i.e. relatively low homology) between different seasonal strains of viral antigens or when there is a pandemic outbreak of a virus for which no standards are yet available.

Such a pandemic outbreak occurred in April 2009, when there was an outbreak in Mexico, the United States, and several other nations of pandemic Influenza A/California/07/2009 H1N1, a novel flu strain evolved that combined genes from human, pig, and bird flu, initially dubbed "swine flu." In this particular case, vaccines were needed before WHO had available standards for the H1 antigen. In September 2009, the US Food and Drug Administration approved four vaccines against the 2009 H1N1 Influenza virus. At the time of the development of these vaccines, however, there still were no WHO standards available to quantify HA in the new vaccines.

For several decades, the HA content of Influenza vaccines has been assayed using Single Radial Immunodiffusion (SRID or SRD) with international standards supplied by World Health Organization (WHO) Collaborating Centers. These international standards are used for the determination of the antigen value, e.g. HA content of vaccines. In SRID, Influenza virions are disrupted by detergent, and submitted to immunodiffusion for three days at room temperature in antibody-loaded agarose gels. Upon gel staining, the precipitation zone diameters of antigen-antibody complexes are measured, and the antigen content of virus preparations of a certain subtype is calculated by using a calibration curve obtained with a whole virus reference batch of this subtype with a known HA content. However, SRID is a laborious and low throughput assay. Moreover, sensitivity, accuracy, and precision, especially for non-purified (in-process) Influenza virus is relatively low.

Kapteyn et al. (Vaccine 24:3137-44, 2006; "Kapteyn") published an RP-HPLC assay for quantification of HA in Influenza viral cultures as well as for the identification of HA from individual Influenza strains in trivalent vaccines. However, Kapteyn's method did not quantify HA without a standard. Additionally, Kapteyn used detergent to solubilize antigen and alkylation to prevent proteins with reactive sulfhydryl groups from re-associating and forming complexes. In fact, in Kapteyn's method, HA was completely isolated by dissolving membranes through the use of a strong detergent. Also Kapteyn's method is described not to be suitable for quantifying HA from formalin-inactivated Influenza strains.

Thus, the art to date does not disclose methods for accurately and efficiently determining HA antigen concentration in either crude or purified HA samples, especially in samples that are not processed with detergents or alkylating agents and in the absence of HA protein standards as provided by WHO collaborating centers. Clearly, a strong need in the art exists for robust, accurate and fast methods for reliable isolation and quantification of antigen, including viral antigens such as HA, in vaccine manufacturing before antigen standards are available from WHO collaborating centers. The following disclosure describes the specifics of such methods.

SUMMARY

The methods described herein were developed to provide a means of measuring antigen content in a vaccine in the absence of available antigen standards. Therefore, the invention addresses one or more needs in the art relating to fast and accurate quantification of antigen concentration in a vaccine during the vaccine development and manufacturing process without the need of international standards. Thus, the methods provided herein allow vaccine manufacturers to more quickly produce a vaccine which can be delivered to the public without waiting for WHO to develop and provide a standard.

More specifically, the invention provides fast and robust methods of isolating and accurately quantifying vaccine antigens, which are accurate and reproducible, in the absence of the use of standards. The disclosure is applicable for use with a variety of antigens, thereby providing an improved method in the art of vaccine manufacturing to date.

The invention provides methods for isolating an antigen from a vaccine composition, the method comprising the steps of: (a) solubilizing the antigen in the vaccine composition without a detergent and without an alkylating agent; and (b) isolating the antigen or an antigen subtype by fractionation.

In some aspects, the solubilizing step is carried out by reduction. In some aspects, the reduction comprises treating the vaccine composition with dithiothreitol. In some aspects, the reduction comprises an incubation time from about 5 minutes to about 20 hours. In other aspects, the reduction comprises an incubation time from about 30 minutes to about 2 hours. In more particular aspects, the reduction comprises an incubation time of about 1 hour. In further aspects, the reduction comprises an incubation temperature from about 20° C. to about 100° C. In various aspects, the reduction comprises an incubation temperature from about 50° C. to about 90° C. In certain aspects, the reduction comprises an incubation temperature at about 85° C. In further aspects, the reduction step is pH-controlled. In various aspects, the reduction is carried out at a pH from about pH 6 to about pH 11. In particular aspects, the reduction is carried out at a pH from about pH 7 to about pH 10. In additional aspects, the solubilizing step further comprises denaturing with a chaotropic agent. In various aspects, the chaotropic agent is guanidine hydrochloride, urea, thiourea, lithium, perchlorate, or thiocyanate. In further aspects, the reduction is further carried out by acidification of the antigen or antigen subtype to prevent disulfide bond formation between separated antigen subtypes. In various aspects, the acidification is carried out with phosphoric acid, hydrochloric acid, sulfuric acid, trifluoroacetic acid, pentafluoropropionic acid, heptafluorobutyric acid, or formic acid.

In some aspects, fractionation is carried out by chromatography. In various aspects, the chromatography is high performance liquid chromatography (HPLC), reversed-phase HPLC (RP-HPLC), ion exchange-HPLC (IEX-HPLC), affinity chromatography, hydrophobic interaction chromatography (HIC), or size exclusion chromatography (SEC). In an exemplary aspect, the chromatography is reversed-phase (RP)-HPLC.

The invention further provides methods for quantifying antigen or antigen subtype content in a vaccine composition. Such methods include all of the methods described herein above for isolating an antigen from a vaccine composition, with a further step of quantifying the antigen or antigen subtype. In exemplary aspects, the quantifying step is carried out without using an antigen standard. In various aspects, the quantifying step comprises quantifying antigen by amino acid analysis. In some aspects, the antigen is viral or bacterial. In certain aspects, the antigen is hemagglutinin (HA). In particular aspects, the HA is from an Influenza virus vaccine composition, a measles virus vaccine composition, a parainfluenza virus vaccine composition, or a mumps virus vaccine composition. In some aspects, the vaccine composition is an Influenza virus vaccine composition. In further aspects, the Influenza virus vaccine composition provides protection from an Influenza virus selected from the group consisting of Influenza A and Influenza B. In various aspects, the antigen subtype is any one of Influenza A HA1, HA2, HA3, HA4, HA5, HA6, HA7, HA8, HA9, HA10, HA11, HA12, HA13, HA14, HA15, and HA16 and Influenza B HA. In certain aspects, the antigen subtype is Influenza A HA subtype HA1, HA2, HA3, HA5, HA7, HA9, HA10, or influenza B HA. In an exemplary aspect, the Influenza A HA subtype is HA1. In further aspects, the Influenza vaccine composition provides protection from an Influenza type selected from the group consisting of Influenza A H1N1, H1N2, H2N2, H3N2, H5N1, H7N1, H7N2, H7N3, H7N7, H9N2, H10N7, and Influenza B. In various aspects, the method quantifies antigen content with a relative standard deviation (RSD) of less than about 2.5%. In more particular aspects, the RSD is about 2.2%. In even more particular aspects, the RSD is about 1.3%.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

DETAILED DESCRIPTION

The disclosure provides a novel method for isolating and preparing antigen and determining antigen concentration in vaccine development and manufacturing in the absence of international standards, for example, World Health Organization (WHO) International Standards, which are biological reference preparations with defined biological activity. The method includes improvements over the prior art by solubilizing antigen from virus in a vaccine composition without the use of detergent and without the use of alkylation. Solubilized antigen is then separated by fractionation and quantified by quantitative amino acid analysis.

The timely availability of WHO International Standards serve as a basis for comparison of biological measurements in vaccine manufacturing worldwide. However, these WHO International Standards are not readily available when there is an outbreak of a new virus and standards need to be prepared. The problem to date is that vaccine manufacturers are forced to quickly develop and produce a new vaccine in response to an outbreak of a new virus while waiting for delivery of WHO International Standards to quantify antigen in their new vaccine. The methods of the present disclosure provide a solution to this problem by providing a new method for quantifying antigen without the need for WHO International Standards.

Another problem to date with methods for separation and retrieval of antigens derived from pathogens is that the separation of antigen from other proteins is not optimal. In the art, there has been poor resolution of the antigen protein peak(s) of interest, recovery was low and not quantitative, and sample preparation times were lengthier. The present disclosure solves many of these problems by using chromatography to isolate antigen in a sample that is denatured and reduced without the use of a detergent and, in exemplary aspects, without alkylation to protect the sulfhydryl groups on the antigen. Thus, sample preparation time is greatly reduced with less side reactions. After isolation of antigen using chromatography, the antigen concentration is quantified without the use of an international standard. In more particular aspects, the quantitative amino acid analysis is carried out as an alternative method of antigen quantification.

The problem to be solved from the prior art was to provide an accurate, rapid and robust method that would be applicable for high-throughput separation, purification, and quantification of an antigen. In more particular aspects, the problem to be solved was to provide such a method without the use of detergents, without the need for alkylation, and without the need for antigen standards. The methods described herein show that the hemagglutinin (HA) antigen, and especially the main determinant HA1, is separated extremely well and with high purity from the other proteins present in the preparation and allows one of skill in the art to determine the amount of antigen present in the preparation, either by comparing it to other (known) values, to internal standards, or by quantitative amino acid analysis.

More particularly, the disclosure relates to a novel method for separating HA antigens, the method comprising the steps of applying a solubilized antigen preparation without a detergent and fractionating the antigen, in one aspect, on a chromatography column. The disclosure, in certain aspects, further includes elution of the HA antigen from the column, and in even further aspects, quantifying the antigen by AAA.

Before any embodiments of the disclosure are explained in detail, however, it is to be understood that the disclosure is not limited in its application to the details of construction and the arrangement of components set forth in the following description or illustrated in the figures and examples. The section headings used herein are for organizational purposes only and are not to be construed as limiting the subject matter described. All references cited in this application are expressly incorporated by reference herein.

The disclosure embraces other embodiments and is practiced or carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

DEFINITIONS

Unless otherwise defined, all technical and scientific terms used herein have the same meaning as commonly understood by one of ordinary skill in the art to which this disclosure belongs.

The following abbreviations are used throughout.
AA Amino acid
AAA Amino acid analysis
DNA Deoxyribonucleic acid
EDTA Ethylenediaminetetraacetic acid
HA Hemagglutinin
HA1-16 Hemagglutinin subtypes1-16
HPLC High Performance Liquid Chromatography
HIC Hydrophobic interaction chromatography
IEX-HPLC Ion Exchange-HPLC
kDa KiloDaltons
LC-MS/MS Liquid chromatography tandem mass spectrometry
MALDI/TOF Matrix-assisted laser desorption ionization/Time-of-Flight mass spectometry
MVB Monovalent bulk
RSD Relative standard deviation
RP-HPLC Reversed-phase HPLC
SDS Sodium dodecyl sulfate
SDS-PAGE Sodium dodecyl sulfate polyacrylamide gel electrophoresis
SEC Size exclusion chromatography
SRD Single radial immundiffusion
UV Ultraviolet It is noted here that, as used in this specification and the appended claims, the singular forms "a," "an," and "the" include plural reference unless the context clearly dictates otherwise.

As used herein, the following terms have the meanings ascribed to them unless specified otherwise.

The terms "polypeptide," "peptide" and "protein" are used interchangeably herein to refer to a polymer of amino acid residues linked via peptide bonds. "Protein" typically refers to large polypeptides. "Peptide" typically refers to short polypeptides.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. The term "almost" is also used interchangeably with the term "approximately." When values are expressed as approximations, by use of the antecedent "about," it will be understood that some amount of variation is included in the range and includes values +/−10%, +/−5%, and +/−1.0% of the disclosed or recited value.

"Influenza" refers to any of three types of Influenza viruses, A, B, and C in the family of Orthmyxoviridae. Only Influenza A and B lead to seasonal outbreaks. Influenza viruses infect their host by binding through hemagglutinin (HA) onto sialic acid sugars on the surfaces of epithelial cells, typically in the nose, throat and lungs of mammals and in the intestines of birds.

The Influenza A genus has one species, Influenza A virus. Influenza A is divided into subtypes or serotypes based on the serological properties of the HA protein (H1-16) and the neuraminidase protein (N1-9). Influenza subtypes are named according to the combination of hemagglutinin and neuraminidase, e.g., HxNy. The subtypes that have been confirmed in humans, ordered by the number of known human pandemic deaths include, but are not limited to, H1N1, H2N2, H3N2, H5N1, H7N7, H1N2, H9N2, H7N2, H7N3, and H10N7. The Influenza B genus has one species, Influenza B virus. Influenza B mutates at a rate 2-3 times slower than type A and consequently is less genetically diverse, with only one Influenza B serotype. The Influenza C genus has one species, Influenza C virus, which infects humans, dogs and pigs, sometimes causing both severe illness and local epidemics. However, Influenza C is less common than the other types.

The term "antigen" or "antigen subtype" refers to a molecule or a portion of a molecule capable of being bound by a selective binding agent, such as an antibody, and additionally capable of being used in a subject to produce antibodies capable of binding to an epitope of each antigen. An antigen, in various aspects, has one or more epitopes. In an exemplary aspect, HA is the antigen. HA is an antigenic glycoprotein that is responsible for binding the virus to the cell that is being infected. There are at least 17 different HA antigens identified to date, labeled HA1-HA16 or, alternatively, H1-H16 for Influenza A, and at least one known HA antigen for Influenza B. H1, H2, and H3, are commonly found in human Influenza A and Influenza B HA antigen is commonly found in human influenza B. The disclosure includes methods of isolating and quantifying all known and yet unknown HA viral proteins including, but not limited to any of HA1, HA2, HA3, HA4, HA5, HA6, HA7, HA8, HA9, HA10, HA11, HA12, HA13, HA14, HA15, HA16 and Influenza B HA.

The term "antigen content" or "antigen concentration" refers to the amount of antigen, i.e. the concentration of antigen, in a sample of vaccine.

The terms "vaccine" or "vaccine composition" refer to a biological preparation that improves immunity to a particular disease (e.g., Influenza). The terms "vaccine" or "vaccine composition" are used interchangeably herein to describe all vaccine formulations including instream-, upstream-, and downstream-process preparations involved in vaccine development and manufacturing.

The term "standard" or "international standard" or "international reference standard" or "antigen standard" refers to a biological reference preparation with defined biological activity as provided by a regulatory authority, e.g., by the World Health Organization (WHO) or a WHO Collaborating Center.

"Relative standard deviation," "RSD," or "% RSD" is the absolute value of the coefficient of variation. It is often expressed as a percentage. A similar term that is sometimes used is the relative variance which is the square of the coefficient of variation. Also, the relative standard error is a measure of a statistical estimate's reliability obtained by dividing the standard error by the estimate; then multiplied by 100 to be expressed as a percentage. The RSD is widely used in analytical chemistry to express the precision and repeatability of an assay. RSD=(standard deviation of array X)×100/(average of array X).

The section headings are used herein for organizational purposes only, and are not to be construed as in any way limiting the subject matter described.

Isolating Antigen from a Vaccine

The disclosure includes methods for isolating antigen including, but not limited to, HA antigens from a vaccine composition. In exemplary embodiments, influenza virus vaccine is obtained from an—upstream, instream, or downstream process of either egg-derived material or virus material from cell culture. Antigen is then solubilized from the vaccine composition without detergent.

Antigen solubilization, also known as virus disintegration, involves the breakdown of virus using chemical or physical methods to isolate an antigen or antigens for further isolation and quantification. In an exemplary aspect, the solubilizing step is carried out by reduction without the use of detergent. Detergents are not used in the methods described herein because they bind to proteins and alter their properties, i.e. detergents contaminate isolated antigen and interfere with chromatographic separation necessary for accurate determination of antigen concentration.

Thus, antigen solubilization is carried out by any reducing agent that is not a detergent that reduces the disulfide bonds of proteins. Suitable reducing agents include, but are not limited to, dithiothreitol (DTT), tris[2-carboxyethyl]phosphine hydrochloride (TCEP), Protein-S—S-Reductant™ (G Biosciences®, Maryland Heights, Mo.), β-Mercaptoethanol, β-Mercaptoethylamine, thiopropyl-agarose, sodium borohydride, sodium cyanoborohydride, sodium phosphorothioate, sulfite and sulfite generating agents, dithioerythritol, tributyl phosphine, glutathione, thioglycolate, 2,3-dimercaptopropanol, or performic acid. In various aspects, guanidine hydrochloride or another chaotropic agent such as, but not limited to, urea, thiourea, lithium, perchlorate, and thiocyanate is also used in the solubilization reaction buffer. A chaotropic agent denatures the protein but does not precipitate the protein. Compounds and methods for carrying out the reduction of proteins are well known to one of skill in the art. Specific reduction solutions and conditions are described in more detail herein in the Examples.

In an exemplary aspect, a reducing buffer or reducing agent reduces disulfide bonds between HA molecules into respective subunits, e.g., HA1 and HA2, and releases, for example, HA1 from the virus. In certain aspects, DTT is used at a concentration of about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 35 mM, 40 mM, 45 mM, 50 mM, 55 mM, 60 mM, 65 mM, 70 mM, 80 mM, 85 mM, 90 mM, 95 mM, 100 mM, 150 mM, 200 mM, 250 mM, 300 mM, 350 mM, 400 mM, 450 mM, or 500 mM. In more particular aspects, DTT is used at a concentration, for example, which ranges from about 20 mM to about 100 mM.

In an exemplary aspect, the reduction comprises an incubation time from about 5 minutes to about 20 hours, from about 10 minutes to about 10 hours, or from about 30 minutes to about 2 hours. In aspects, incubation times are about 1 hour. Thus, incubation times are about 5 minutes, about 10 minutes, about 20 minutes, about 30 minutes, about 40 minutes, about 50 minutes, about 1 hour, about 1.5 hours, about 2 hours, about 2.5 hours, about 3 hours, about 3.5 hours, about 4 hours, about 4.5 hours, about 5 hours, about 5.5 hours, about 6 hours, about 6.5 hours, about 7 hours, about 7.5 hours, about 8 hours, about 8.5 hours, about 9 hours, about 9.5 hours, about 10 hours, about 11 hours, about 12 hours, about 13 hours, about 14 hours, about 15 hours, about. 16 hours, about 17 hours, about 18 hours, about 19 hours, or about 20 hours. Specific reduction times are described in more detail herein in the Examples.

In other aspects, the reduction comprises an incubation temperature from about 20° C. to about 100° C. In particular aspects, the reduction comprises an incubation temperature from about 50° C. to about 90° C. In more particular aspects, the reduction comprises an incubation temperature at about 85° C. Thus, incubation temperatures are about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. Specific reduction temperatures are described in more detail herein in the Examples.

In further aspects, the reduction of antigen is pH-controlled. In various aspects, the reduction reaction is carried out at a pH from about pH 6 to about pH 11. In particular aspects, the pH is from about pH 7 to about pH 10. In more particular aspects, the pH is about 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In an exemplary aspect, reduction is carried out without alkylation. Alkylation protects the sulfhydryl groups of proteins after reduction and prevents back reaction of free cysteines. Thus, alkylation is typically used to prevent re-association and/or complex formation of separated HA antigens, e.g., HA1 and HA2, and other proteins. The use of alkylating agents, like 4-vinylpyridine, however, decreased protein purity as described in more detail herein in the Examples. Thus, to prevent re-association and/or complex formation of separated antigens, e.g., HA1 with HA2, and other proteins, the sulfhydryl groups of all proteins are protected without the use of an alkylating agent.

In an exemplary aspect, to prevent re-association and/or complex formation of separated antigens and other proteins without further use of an alkylating agent, reduced protein sulfhydryl groups are protected by protonation by acidification. Acidification prevents disulfide bond formation because for disulfide bonds to form, a sulfhydryl group needs to be at least partially in the ionic form. Acidification is a simple and effective treatment, wherein pH is monitored and adjusted to prevent precipitation of antigen. In various aspects, acidification is carried out with phosphoric acid, hydrochloric acid, sulfuric acid, trifluoroacetic acid, pentafluoropropionic acid, heptafluorobutyric acid, or formic acid. In exemplary aspects, acidification is carried out with phosphoric acid; however, the use of phosphoric acid is not limiting, as all other methods of acidification in the art are used. Methods for acidification are well known in the art and are not elaborated herein further. Specific acidification solutions and conditions are described in more detail herein in the Examples.

Antigen Fractionation

After reduction and acidification, antigen is isolated by fractionation. In exemplary aspects, fractionation is carried out by chromatography. Any suitable type of chromatography known in the art is used. For example, such suitable types of chromatography include, but are not limited to, high performance liquid chromatography (HPLC), reversed-phase HPLC (RP-HPLC), ion exchange-HPLC (IEX-HPLC), affinity chromatography, hydrophobic interaction chromatography (HIC), or size exclusion chromatography (SEC).

In some aspects, antigen fractionation is carried out by RP-HPLC. Therefore, suitable types of reversed-phase columns include, but are not limited to, silica columns or polymer-based columns, porous, non-porous or monolithic, with various modifications ranging from C2 to C18. Column diameter suitable for analytical purposes is typically, but not limited to, a range from about 75 µm to about 5 mm, depending on the flow rate, which can range variously from about 0.1 µl/min to about 5 ml/min. For isolation of a sufficient amount of antigen, columns with a diameter from about 1 mm to about 10 mm are typically used. Proteins are separated and eluted from reversed-phase columns with mixtures of aqueous and organic solvents such as, but not limited to, acetonitrile, methanol, ethanol, butanol, propanol, isopropanol, and terahydrofuran, and often containing modifiers such as, but not limited to, hydrochloric acid, sulfuric acid, trifluoroacetic acid, pentafluoropropionic acid, heptafluorobutyric acid, formic acid, phosphoric acid, and phosphate buffers. Methods for reversed-phase HPLC of proteins are well known in the art and are not elaborated herein further as they can be carried out by one skilled in the art. Specific reversed-phase HPLC methods and conditions are described in more detail herein in the Examples.

Antigen fractionation by chromatography, as described herein in the Examples, provided excellent linearity and precision with low relative standard deviation (RSD). Linearity, the ability (within a certain range) to obtain test results which are directly proportional to the concentration (amount) of analyte in the sample, is important in any analytical procedure. The precision of an analytical procedure expresses the closeness of agreement (degree of scatter) between a series of measurements obtained from multiple sampling of the homogeneous sample under the prescribed conditions. Precision, in various aspects, is considered at three levels: repeatability, intermediate precision and reproducibility.

Antigen Quantification

Methods for quantifying antigen or antigen subtype after isolation by fractionation without the use of international standards are included in the disclosure. Suitable methods for quantifying fractionated antigen include, but are not limited to, amino acid analysis (AAA), nitrogen determination (Kjeldahl), mass spectrometry, and isotope dilution mass spectrometry.

In an exemplary aspect, antigen concentration is determined using AAA. AAA refers to the methodology used to determine the amino acid composition and/or quantify the concentration of antigen in a composition based on the molecular weight of the antigen and the amino acids. AAA is carried out using conventional techniques known to those with skill in the art. AAA is a suitable tool for precise determination of protein quantities, but also provides detailed information regarding the relative amino acid composition and free amino acids. See *Amino Acid Analysis Protocols: Methods in Molecular Biology, Volume* 159 (edited by Cooper et al., © 2001 Humana Press Inc., Totawa, N.J.). The relative amino acid composition gives a characteristic profile for proteins, which is often sufficient for identification of a protein. It is often used as decision support for choice of proteases for protein fragmentation.

Typically, AAA includes hydrolysis, and then separation, detection and quantification. Hydrolysis or "acid hydrolysis" is typically achieved by acid conditions. For example, a standard procedure is hydrolysis with 6 M hydrochloric acid (24 hours, 110° C.). This standard procedure is a compromise between time requirement and temperature and can be modified by one of skill in the art. In exemplary aspects, a hydrolysis time study is carried out to determine optimal hydrolysis time for HA. Hydrolysis time can be optimized, however, for each individual antigen that is quantified according to the methods of the disclosure. Procedures for AAA are well known in the art and products for AAA are commercially available (AccQ Tag kit (Waters, No WAT052880) and Sigma-Aldrich). In some embodiments, Zorbax Eclipse AAA HPLC Columns are used. One of ordinary skill in the art is aware of various methods to carry out AAA. Specific AAA procedures are described in more detail herein in the Examples.

Based on the known sequence for a particular antigen, the theoretical number of amino acids per antigen molecule and, subsequently, the molar amount of antigen per injection are calculated. Calculated or measured molecular mass of antigen and the applied dilution factors during the sample preparation allow for the calculation of the antigen concentration in the sample, expressed as µg antigen per mL of sample.

In an exemplary aspect, a formula for calculating HA concentration is provided herein below.

$$n_{HA1} = n_{AA}/x_{AA}$$

$n_{HA1}$ ... molar amount of hemagglutinin HA1 [µmol]
$n_{AA}$ ... molar amount of individual amino acid (result from amino acid analysis) [µmol]
$x_{AA}$ ... number of individual amino acid per molecule of hemagglutinin HA1

$$n_{HA1} = n_{HA}$$

$n_{HA}$ ... molar amount of hemagglutinin [µmol]

$$m_{HA} = n_{HA} * M_{HA}$$

$n_{HA}$ ... molar amount of hemagglutinin [µmol]
$m_{HA}$ ... mass of HA [µg]
$M_{HA}$ ... Molecular mass of hemagglutinin (calculated or determined) [µg*µmol$^{-1}$]

$$c_{HA} = m_{HA} * DF/V_i$$

$c_{HA}$ ... concentration of hemagglutinin [µg/ml]
DF ... dilution factor
$V_i$ ... injection volume [ml]

In an exemplary embodiment of the disclosure, the quantification of HA is based on the peak area of HA1, which is well separated from the other vaccine components. The applicability of the present disclosure has been demonstrated for different Influenza A subtypes including, but not limited to H1N1, H3N2, H5N1, H9N2, and Influenza B, strongly suggesting that the methods disclosed herein can be broadly applied for different HA antigens. The disclosure has been described in detail for HA from Influenza but is not to be limited to the use of HA from Influenza alone. The disclosure is also applicable for HA antigens from other viruses and for the separation and quantification of other antigens or antigen subtypes.

The methods of determining antigen concentration in a vaccine composition described herein measure antigen concentration with an RSD of less than about 5%, less than about 4%, less than about 3%, less than about 2.9%, less than about 2.8%, less than about 2.7%, less than about 2.6%, less than about 2.5%, less than about 2.4%, less than about 2.3%, less than about 2.2%, less than about 2.1%, less than about 2.0%, less than about 1.9%, less than about 1.8%, less than about 1.7%, less than about 1.6%, less than about 1.5%, less than about 1.4%, less than about 1.3%, less than about 1.2%, less than about 1.1%, and less than about 1.0%. In exemplary aspects, the methods described herein measure antigen concentration with an RSD of about 2.2% and about 1.3% depending on the antigen concentration.

Each publication, patent application, patent, and other reference cited herein is incorporated by reference in its entirety to the extent that it is not inconsistent with the present disclosure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Additional aspects and details of the disclosure will be apparent from the following examples, which are intended to be illustrative rather than limiting.

Example 1

Developing and Optimizing a Method for the Isolation and Quantification of HA in a Vaccine The objective of the experiments described herein was to develop a new HPLC method for measuring total HA content of vaccine preparations of Influenza A/California/07/2009 (H1N1) based on the measurement of HA (i.e. HA1) when no standard reagents are available from WHO or elsewhere.

The following batches of new product of Influenza A/California/07/2009 (H1N1) were evaluated:

TABLE 1

Test and reference items

| Sample | Remarks | Protein content (µg/ml) |
|---|---|---|
| 1 | Small scale batch | 149 |
| 2 | Large scale batch | 530 |
| 3 | Large scale batch | 373 |

Quantification of HA by Reversed Phase HPLC

Sample preparation conditions were optimized as follows. Undiluted samples or samples diluted with deionized water were mixed with the same volume of reducing buffer (6M guanidine hydrochloride, 266 mM Tris/HCl, 1 mM EDTA, pH 8.3, and 40 mM dithiothreitol). Samples were incubated at 85° C. for one hour, followed by addition of 10% (v/v) 8.5% phosphoric acid to stop the reaction and prevent back reaction, the formation of disulfide bonds from free cysteines. Samples were centrifuged at 18,407 g for 10 min to remove any particulate matter. Identical HPLC conditions were used.

An Agilent HPLC system equipped with a quaternary pump and a diode array detector was used. Proteins were separated by reversed phase-HPLC on a Jupiter 5µ C4 column (150×2 mm) using the following gradient:
Eluent A: 0.1% trifluoroacetic acid in water
Eluent B: 0.085% trifluoroacetic acid in acetonitrile
Eluent C: methanol Samples and standards were injected by a separate method with an isocratic elution at 20% Eluent B at a flow rate of 0.4 ml/min for 10 min. This was followed by the method for elution of the proteins:

TABLE 2

Gradient for HPLC analysis

| Time | Eluent A | Eluent B | Eluent C | Flow rate |
|---|---|---|---|---|
| 0 min | 80% | 20% | 0% | 0.4 ml/min |
| 15 min | 58% | 42% | 0% | |
| 20 min | 0% | 100% | 0% | |
| 21 min | 0% | 0% | 100% | |
| 24 min | 0% | 0% | 100% | |
| 25 min | 80% | 20% | 0% | |
| 40 min | | stop | | |

Eluted proteins were detected using UV absorption at 214 nm. HA1 was quantified and expressed as µg HA per ml of sample. Due to the absence of a proper standard, initially only the area was reported. This was followed by quantification of eluted HA1 by amino acid analysis for sample 2. The monovalent bulk (MVB) sample preparation (sample 1) was used as reference preparation for further calibration of HPLC analyses.

Amino Acid Analysis

Acid hydrolysis of protein was carried out in glass ampoules. 2 nmol of 2-L-amino butyric acid was added to each ampoule as an internal standard and HPLC fractions were collected directly into the ampoules. Collected fractions were dried under vacuum (SpeedVac, Savant, SVC100H). Samples were dissolved in 300 µl 6N hydrochloric acid/0.2% Phenol, overlaid with nitrogen, and ampoules were heat-sealed. Acid hydrolysis was carried out at 115° C. for 18 h. Ampoules were opened. 500 µl deionized water was added. The solution was filtered (0.2µ) transferred into Eppendorf® vials and dried under vacuum (SpeedVac, Savant, SVC100H). Amino acid analysis was carried out using the AccQ Tag kit (Waters, No WAT052880) according to the manufacturer's instructions. Briefly, samples were dissolved in 0.1 N hydrochloric acid and amino acids were labeled using the AccQ Fluor Reagent. Internal standard (α-amino butyric acid) and amino acid standard (Agilent, No. 5061-3330) were treated the same way.

A Waters HPLC system equipped with a quaternary pump and a fluorescence detector (Spectra Systems FL 2000) were used. Amino acids were separated by reversed phase-HPLC on an AccQ Tag C18 column (4µ, 150×3.9 mm, Waters, No. WAT052885) equipped with a Sentry Guard Column (20×3.9 mm, Waters, No. WAT044380) and precolumn (150×2 mm) operated at 37° C. 5 µl of sample were injected and amino acid profile was analyzed using the following gradient:
Eluent A: Deionized water
Eluent B: Acetonitrile, gradient grade
Eluent C: AccQ-Tag buffer concentrate (Waters, No. WAT052890) diluted 1:10 in deionized-water

TABLE 3

Gradient for amino acid analysis

| Time | Eluent A | Eluent B | Eluent C | Flow rate |
|---|---|---|---|---|
| 0 min | 0% | 0% | 100% | 1 ml/min |
| 0.5 min | 0% | 1% | 99% | |
| 18 min | 0% | 5% | 95% | |
| 19 min | 0% | 9% | 91% | |
| 29.5 min | 0% | 17% | 83% | |

TABLE 3-continued

Gradient for amino acid analysis

| Time | Eluent A | Eluent B | Eluent C | Flow rate |
|------|----------|----------|----------|-----------|
| 33 min | 40% | 60% | 0% | |
| 36 min | 0% | 0% | 100% | |
| 60 min | | stop | | |

Eluting fluorescent-labeled amino acids were detected using fluorescence detection with excitation at 250 nm and emission at 394 nm. Calibration was carried out using an external standard (Agilent, No. 5061-3330) and corrected using an internal standard. Data were further processed for leucine, valine, lysine and phenylalanine, as these are the most stable amino acids under acid hydrolysis conditions.

Based on the known sequence for HA of Influenza A/California/07/2009 (H1N1) (GenBank accession No. ACQ55359.1), the theoretical number of amino acids per HA1 molecule and, subsequently, the molar amount of HA per injection were calculated. Calculated or measured molecular mass of HA and the applied dilution factors during the sample preparation allowed for the calculation of the HA concentration in the sample, expressed as µg HA per ml of sample.

SDS-PAGE

Samples were analyzed by sodium dodecyl sulfate-polyacrylamide gel electrophoresis (SDS-PAGE) followed by Coomassie Blue staining. Monovalent bulk samples were analyzed under reducing and non-reducing conditions and compared to reduced HA1 isolated by HPLC. After electrophoresis, the gel was stained for 2 hours with the ready-to-use Coomassie solution (GelCode® Blue Stain Reagent, Pierce, cat. #24590). The gel was destained with 2-3 changes of deionized water and kept in deionized water overnight before image scanning. The SDS-gel was scanned with the GelData program provided by the manufacturer of the densitometer Image Scanner III (GE Healthcare). The Image Quant TL software (Amersham Bioscience) was used to identify the bands and to obtain the optical density of the absorption. The limits of the bands were set manually.

MALDI/TOF

For matrix-assisted laser desorption/ionization time of frame (MALDI/TOF) analyses, proteins were purified using HPLC by the method described above. The lyophilized HPLC fraction was dissolved in 5 µl 50% acetonitrile, 0.5% formic acid in water and mixed with matrix solution (10 mg/ml sinapinic acid in 50% acetonitrile, and 0.5% formic acid in water). 1 µl was deposited on a MALDI/TOF target and dried at room temperature. Spectra were acquired on an Applied Biosystems 4800 MALDI TOF/TOF using either the standard multiple channel plate detector or a CovalX HM1 high mass detector.

Spectra were analyzed using the provided software package (Data Explorer 4.9, Applied Biosystems). Molecular mass was calculated as a mean of at least 10 spectra acquired with external calibration done with bovine serum albumin.

Identification of Peaks by LC-MS/MS

HPLC peaks were manually collected and lyophilized in a SpeedVac. Lyophilisates were dissolved in reconstitution buffer (8M urea, 100 mM ammonium bicarbonate, pH 8.4), diluted to a final concentration of 0.9M urea by addition of 100 mM ammonium bicarbonate, pH 8.4, and digested using trypsin.

For in-gel trypsin digestion, gel slices were cut from the SDS-PAGE gels and repeatedly washed by acetonitrile followed by 100 mM ammonium bicarbonate, pH 8.4, and again acetonitrile. As a last step, gel slices were treated with acetonitrile and lyophilized in a SpeedVac for 1 h. Gel slices were rehydrated using trypsin solution (12.5 ng/µl) and digested overnight. Peptides were then recovered from the supernatant.

The generated peptides were separated on an Agilent 1100 capillary HPLC using a Zorbax SB300 C18 5µ 150×0.5 mm column and analyzed online using liquid chromatography-mass spectrometry with peptide mass fingerprinting (LC-MS/MS or tandem MS) on a linear trap quadrupole (LTQ or linear ion trap) Orbitrap mass spectrometer equipped with an electrospray source. Peptides were measured in a precursor scan in the LTQ Orbitrap with accurate mass and a resolution of 60,000. Subsequently, the four most intense ions were selected and analyzed using tandem mass spectrometry (MS/MS) mode in the LTQ. MS/MS spectra were processed for identification using Bioworks 3.3 software and searched against a manually made database containing viral protein from H1N1 only (sequences retrieved from Influenza Virus Resource, 15 May 2009) or against Uniprot database (Release 14.8, 10 Feb. 2009). Relative quantification was carried out using the height of peaks in reconstructed ion chromatograms for the identified peptides.

HPLC Method Optimization

Initial experiments on H1N1 were carried out using the established HPLC method for quantification of HA in other Influenza vaccines. Briefly, the sample preparation included a virus disintegration step at 37° C. for 1 h followed by alkylation with 4-vinylpyridine. Using this sample preparation method, HA1 was isolated by fractionation of the HPLC peak from sample 2 and quantified using amino acid analysis. As a mean of a six-fold determination of the amino acid analysis, a value of 62.2 µg/ml HA was obtained in sample 1. SDS-PAGE was used to estimate recovery of HA1 from the sample. The gels were Coomassie stained and evaluated by densitometric scanning. Results indicated that the isolated HA1 migrating at 53 kDa had only about 13% of the intensity of the corresponding band in sample 1. LC-MS/MS analyses were used to determine the purity of this band in sample 1. These analyses provided an HA1 content in this band of approx. 25% (n=6), whereas the main content was nucleoprotein. Taken together, results showed that the recovery of HA1 was only about 50%. Due to the low recovery of HA1, further optimization of the sample preparation was undertaken.

Incubation temperatures during the virus disintegration step were varied and highest values of recovery were found for temperatures at about 80° C. Further experiments included optimization of incubation temperature for virus disintegration between 37° C. and 90° C. and optimization of incubation times between 30 min and 4 h. In addition, as an alternative for the alkylation step, acidification with 8.5% phosphoric acid was investigated.

The optimal conditions for virus disintegration, i.e., solubilization, were found to be about 85° C. for 1 h followed either by the alkylation step or by the acidification step. Using these optimized sample preparation conditions, HA1 recovery was again checked by SDS-PAGE. HA1 recovery was determined to be between 90 and 120% based on HA1 content in the corresponding band in sample 1 of 25%.

In addition to HA1 recovery, specificity was checked for the two optimized methods (with and without alkylation). By LC-MS/MS analyses, protein purity in the HA1 peak for the method with alkylation with 4-vinylpyridine was determined to be 87%. In contrast, if acidification with phosphoric acid instead of alkylation was used to prevent back reaction of free cysteines, protein purity in the HA1 peak improved to 96%.

Establishment of a Reference Preparation
Sequence Alignment

Sequences with the following accession numbers were retrieved from Genbank: (1) HA, Influenza A virus (A/California/07/2009(H1N1)): ACQ55359.1; and (2) HA, Influenza A virus (A/Solomon Islands/03/2006(H1N1)), ABU50586.1. Protein sequences were aligned using ClustalW with default settings.

According to sequence alignment homology of Influenza A virus (A/California/07/2009(H1N1)) HA and Influenza A virus (A/Solomon Islands/03/2006(H1N1)) HA, HA homology is only about 79% between these two viruses. Other interpandemic strains show comparable low homology to A/California/07/2009(H1N1). This low homology suggested that calibration with an interpandemic reference antigen was not possible in the case of the pandemic H1N1 strain.

Molecular Mass by MALDI/TOF

Theoretical molecular mass of Influenza A virus (A/California/07/2009(H1N1)) HA based on amino acid sequence (accession number: HA, Influenza A virus (A/California/07/2009(H1N1)): ACQ55359.1) is 61424 (HA0, disulfide bonds reduced, comprises HA1 and HA2 that is not proteolytically cleaved), 36312 for reduced HA1, and 25130 for reduced HA2. However, this does not include post-translational modification, such as glycosylation, especially N-glycosylation (5 potential N-glycosylation sites were observed in the HA1 domain) which contributes considerably to glycoprotein mass. The molecular mass of isolated HA1 after reduction was measured using MALDI/TOF to be 45268±119 (n=15) as measured for sample 2. For sample 3, an HA1 molecular mass of 45229±101 (n=20) was measured. Within the error of the method, there was no difference in molecular mass of HA1 between these two lots. The MALDI/TOF data were further supported by LC-MS peptide mapping data where the glycopeptides were analyzed after trypsin digestion of the viral proteins.

TABLE 4

Glycopeptides identified by LC-MS peptide mapping in HA1 (numbering of amino acids excluding signal peptide)

| Glycosylated amino acid | Consensus sequence | Main isoform | Molecular mass (average) |
|---|---|---|---|
| N10 or N11 | NNST | Complex type, triantennary, core fucosylated | 2135.0 |
| N23 | NVT | Complex type, biantantennary, core fucosylated | 1769.6 |
| N87 | NGT | High mannose type, Man7 | 1541.4 |
| N278 | NTT | Complex type, biantennary | 1623.5 |

TABLE 4-continued

Glycopeptides identified by LC-MS peptide mapping in HA1 (numbering of amino acids excluding signal peptide)

| Glycosylated amino acid | Consensus sequence | Main isoform | Molecular mass (average) |
|---|---|---|---|
| N287 | NTS | Complex type, biantennary | 1623.5 |

These N-glycosylation results demonstrated good agreement with the difference between measured molecular mass by MALDI/TOF and theoretical molecular mass. For mass calculation, the molecular mass by MALDI/TOF was used, as this measurement is based on a mean of the different N-glycosylation isoforms.

TABLE 5

Glycopeptides identified by LC-MS peptide mapping in HA2 (numbering of amino acid excluding signal peptide)

| Glycosylated amino acid | Consensus sequence | Main isoform | Molecular mass (average) |
|---|---|---|---|
| N462 | NGT | Complex type, biantennary, core fucosylated | 1769.6 |

HA2 could not be isolated and, therefore, molecular mass could not be measured by MALDI/TOF. However, N-glycosylation could be identified by LC-MS peptide mapping (Table 5). For calculation, the theoretical molecular mass of HA2 (25130) was used and the molecular mass of the identified N-glycosylation was added to yield a mass of 26900. According to these values for HA1 and HA2, the total molecular mass of HA, including glycosylated HA1, glycosylated HA2, and 6 disulfide bonds is 72156.

Amino Acid Analysis

Amino acid analysis was carried out after optimization of sample preparation in parallel for two options of sample preparation either (1) including an alkylation step with 4-vinylpyridine, or (2) including an acidification step with phosphoric acid. Sample 2 was used as a reference preparation for calibration of HPLC analysis.

Sample 2 was prepared with an alkylation step as described below to determine how alkylation affected purification. To determine HA content, HA1 fractionation was carried out with a disintegration step at 85° C. for 1 h and alkylation with 4-vinylpyridine. HA1 HPLC peak fractions were collected and used for amino acid analysis. Hydrolysates were analyzed for their content of leucine, valine, lysine and phenylalanine. Calculation of HA concentration was carried out using molecular mass as determined by MALDI/TOF. Mean HA content per peak was 4.64 μg (n=8) corresponding to 93.7±3.2 μg/ml HA. Because HA1 purity was determined to be only 87%, HA value was overestimated and, thus, alkylation was not considered useful for further analysis.

TABLE 6

Amino acid data based on sample preparation of sample 2 with disintegration at 85° C. for 1 h and alkylation with 4-vinylpyridine

| | 85° C. + 4VP_2 (mg/peak) | 85° C. + 4VP_3 (mg/peak) | 85° C. + 4VP_4 (mg/peak) | 85° C. + 4VP_5 (mg/peak) | 85° C. + 4VP_6 (mg/peak) | 85° C. + 4VP_7 (mg/peak) |
|---|---|---|---|---|---|---|
| L-Valine | 4.47 | 4.60 | 4.52 | 4.71 | 4.32 | 4.60 |
| L-Lysine HCl | 4.09 | 4.19 | 4.23 | 4.36 | 3.96 | 4.17 |
| L-Leucine | 4.61 | 4.73 | 4.66 | 4.88 | 4.42 | 4.71 |

TABLE 6-continued

Amino acid data based on sample preparation of sample 2 with disintegration at 85° C. for 1 h and alkylation with 4-vinylpyridine

| | 85° C. + 4VP_2 (mg/peak) | 85° C. + 4VP_3 (mg/peak) | 85° C. + 4VP_4 (mg/peak) | 85° C. + 4VP_5 (mg/peak) | 85° C. + 4VP_6 (mg/peak) | 85° C. + 4VP_7 (mg/peak) |
|---|---|---|---|---|---|---|
| L-Phenylalanine | 4.92 | 5.09 | 4.98 | 5.25 | 4.78 | 5.04 |
| Mean | 4.52 | 4.65 | 4.60 | 4.80 | 4.37 | 4.63 |
| Standard deviation | 0.34 | 0.37 | 0.31 | 0.37 | 0.34 | 0.36 |
| RSD % | 7.62 | 8.00 | 6.79 | 7.70 | 7.72 | 7.70 |
| Peak equals XXµl MVB | 49.50 | 49.50 | 49.50 | 49.50 | 49.50 | 49.50 |
| HA (µg/ml) in MVB | 91.35 | 93.94 | 92.89 | 96.93 | 88.27 | 93.49 |
| HA (µg/ml) in MVB | 93.7 | | | | | |
| Number | 8 | | | | | |
| Standard deviation | 3.2 | | | | | |
| RSD % | 3.4 | | | | | |

Sample 2 was also prepared with an acidification step. To determine HA content of sample 2, fractions containing HA1 were prepared including a disintegration step at 85° C. for 1 h and an acidification step with phosphoric acid. HA1 HPLC peak fractions were collected and used for amino acid analysis. The hydrolysates were analyzed for their content of leucine, valine, lysine, and phenylalanine. Calculation of HA concentration was carried out as described herein using the molecular mass determined by MALDI/TOF. Mean HA content per peak was 4.21 µg (n=8) corresponding to 92.7±9.0 µg/ml HA. This value was used for further calibration of HA HPLC determination. Fractionation of HA1 was then carried out for amino acid analysis.

Final Method

Table 8 summarizes the main parameters checked for development of a new sample preparation method. A final decision on which method to use was made mainly based on specificity using LC-MSMS, where the method comprising alkylation with 4-vinyl pyridine showed considerably lower specificity. This observation was most probably due to the changed elution position, as modification slightly increases hydrophilicity. The changed elution position resulted in a difference of coeluting proteins. HA1 elution profiles for sample preparations, with or without alkylation, were carried out. HA content in a sample prepared with alkylation with 4-vinylpyridine was determined to be slightly greater, possibly due to a greater concentration of contaminating proteins.

TABLE 7

Amino acid data based on sample preparation with disintegration at 85° C. for 1 h and acidification using phosphoric acid

| Sample name | 85° C. + 4VP_2 (mg/peak) | 85° C. + 4VP_3 (mg/peak) | 85° C. + 4VP_4 (mg/peak) | 85° C. + 4VP_5 (mg/peak) | 85° C. + 4VP_6 (mg/peak) | 85° C. + 4VP_7 (mg/peak) |
|---|---|---|---|---|---|---|
| L-Valine | 4.80 | 4.33 | 4.26 | 4.16 | 3.90 | 3.81 |
| L-Lysine HCl | 4.45 | 3.94 | 3.84 | 3.79 | 3.56 | 3.40 |
| L-Leucine | 5.34 | 4.68 | 4.46 | 4.35 | 4.07 | 3.93 |
| L-Phenylalanine | 5.55 | 4.91 | 4.69 | 4.54 | 4.22 | 4.06 |
| Mean | 5.03 | 4.47 | 4.31 | 4.21 | 3.94 | 3.80 |
| Standard deviation | 0.50 | 0.42 | 0.36 | 0.32 | 0.28 | 0.29 |
| RSD % | 10.00 | 9.51 | 8.40 | 7.62 | 7.21 | 7.54 |
| Peak equals XXµl MVB | 45.45 | 45.45 | 45.45 | 45.45 | 45.45 | 45.45 |
| HA (µg/ml) in MVB | 110.75 | 98.25 | 94.92 | 92.63 | 86.60 | 83.62 |
| HA (µg/ml) in MVB | 92.7 | | | | | |
| Number | 8 | | | | | |
| Standard deviation | 9.0 | | | | | |
| RSD % | 9.7 | | | | | |

TABLE 8

Comparison of the main method development parameters for two sample preparations.

| | Option 1 | Option 2 |
|---|---|---|
| Reduction | 85° C., 1 h | 85° C., 1 h |
| Alkylation | 4-vinylpyridine | No alkylation, acidification using phosphoric acid |
| Sample 2 HA by AAA | 93.7 µg/ml | 92.7 µg/ml |
| Specificity by SDS-PAGE | Single band at 53 kDa | Single band at 53 kDa |
| Specificity by LC-MSMS | 87% | 96% |
| Recovery of HA1 from virus | | 90-120% |

For all following experiments, sample preparation was carried out according to the optimized methods described in the initial experiments above.

Method Qualification

Linearity

One of the key criteria of an analytical procedure is linearity, the ability (within a certain range) to obtain test results that are directly proportional to the concentration (amount) of analyte in the sample. To prove linearity of the concentration-dependent HPLC response, sample 2 was diluted to different concentrations with deionized water, and samples at different concentrations were analyzed by RP-HPLC. The concentration of the reference preparation was determined by amino acid analysis as described above.

TABLE 9

HA quantification with RP HPLC - Linearity

| Level | Protein concentration (µg/ml) | Day 1 (area) | Day 2 (area) | Mean (area) | % RSD |
|---|---|---|---|---|---|
| 1 | 23.175 | 1086.10327 | 1082.69043 | 1093.21676 | 1.95 |
|   | 23.175 | 1070.05615 | 1112.24597 | | |
|   | 23.175 | 1126.27209 | 1081.93262 | | |
| 2 | 30.9 | 1390.47998 | 1437.05981 | 1419.27645 | 1.52 |
|   | 30.9 | 1404.59485 | 1421.58142 | | |
|   | 30.9 | 1449.30212 | 1412.64050 | | |
| 3 | 46.35 | 2089.53711 | 2053.53540 | 2097.28626 | 1.16 |
|   | 46.35 | 2113.89282 | 2097.01416 | | |
|   | 46.35 | 2108.31055 | 2121.42749 | | |
| 4 | 92.7 | 4000.14893 | 4151.25439 | 4074.06832 | 1.26 |
|   | 92.7 | 4047.75854 | 4102.61670 | | |
|   | 92.7 | 4060.75830 | 4081.87305 | | |
| 5 | 139.1 | 6025.29395 | 6045.49121 | 6040.19670 | 0.51 |
|   | 139.1 | 6011.38965 | 6097.27539 | | |
|   | 139.1 | 6042.43066 | 6019.29932 | | |
| 6 | 185.4 | 8058.32422 | 8064.66162 | 7986.82243 | 1.96 |
|   | 185.4 | 8001.92432 | 7980.31494 | | |
|   | 185.4 | 8130.56104 | 7685.14844 | | |

TABLE 10

Test and reference items, Sample 2

| Level | Dilution | Injection volume (µL) | Protein concentration (µg/ml) determined by AAA |
|---|---|---|---|
| 1 | 1:4 | 100 | 23.175 |
| 2 | 1:3 | 100 | 30.9 |
| 3 | 1:2 | 100 | 46.35 |
| 4 | No | 100 | 92.7 |
| 5 | No | 150 | 139.05 |
| 6 | No | 200 | 185.4 |

A calibration curve of the data showed good linearity in the protein concentration range between 23.175 µg/ml and 185.4 µg/ml. Table 11 shows the calculated residues. Every single calculated value lies within ±5% of the theoretical value.

TABLE 11

Residues of calibration curve

| Level | Protein concentration [µg/ml] | Area measured [mAUx*s] | Protein concentration measured [µg/ml] | Residues [µg/ml] | Residues [%] |
|---|---|---|---|---|---|
| 1 | 23.175 | 1086.10327 | 22.80 | −.038 | −1.63 |
|   | 23.175 | 1070.05615 | 22.42 | −.075 | −3.25 |
|   | 23.175 | 1126.27209 | 23.74 | 0.57 | 2.45 |
|   | 23.175 | 1082.69043 | 22.72 | −0.46 | −1.97 |
|   | 23.175 | 1112.24597 | 23.41 | 0.24 | 1.03 |
|   | 23.175 | 1081.93262 | 22.70 | −0.47 | −2.05 |
| 2 | 30.9 | 1390.47998 | 29.96 | −0.94 | −3.06 |
|   | 30.9 | 1404.59485 | 30.29 | −0.61 | −1.98 |
|   | 30.9 | 1449.30212 | 31.34 | 0.44 | 1.42 |
|   | 30.9 | 1437.05981 | 31.05 | 0.15 | 0.49 |
|   | 30.9 | 1421.58142 | 30.69 | −0.21 | −0.69 |
|   | 30.9 | 1412.64050 | 30.48 | −0.42 | −1.37 |
| 3 | 46.35 | 2089.53711 | 46.39 | 0.04 | 0.09 |
|   | 46.35 | 2113.89282 | 46.97 | 0.62 | 1.33 |
|   | 46.35 | 2108.31055 | 46.83 | 0.48 | 1.04 |
|   | 46.35 | 2053.53540 | 45.55 | −0.80 | −1.73 |
|   | 46.35 | 2097.01416 | 46.57 | 0.22 | 0.47 |
|   | 46.35 | 2121.42749 | 47.14 | 0.79 | 1.71 |
| 4 | 92.7 | 4000.14893 | 91.32 | −1.38 | −1.49 |
|   | 92.7 | 4047.75854 | 92.44 | −0.26 | −0.28 |
|   | 92.7 | 4060.75830 | 92.74 | 0.04 | 0.05 |
|   | 92.7 | 4151.25439 | 94.87 | 2.17 | 2.34 |
|   | 92.7 | 4102.61670 | 93.73 | 1.03 | 1.11 |
|   | 92.7 | 4081.87305 | 93.24 | 0.54 | 0.58 |
| 5 | 139.05 | 6025.29395 | 138.94 | −0.11 | −0.08 |
|   | 139.05 | 6011.38965 | 138.61 | −0.44 | −0.32 |
|   | 139.05 | 6042.43066 | 139.34 | 0.29 | 0.21 |
|   | 139.05 | 6045.49121 | 139.41 | 0.36 | 0.26 |
|   | 139.05 | 6097.27539 | 140.63 | 1.58 | 1.13 |
|   | 139.05 | 6019.29932 | 138.79 | −0.26 | −0.18 |
| 6 | 185.4 | 8058.32422 | 186.74 | 1.34 | 0.72 |
|   | 185.4 | 8001.92432 | 185.41 | 0.01 | 0.01 |
|   | 185.4 | 8130.56104 | 188.44 | 3.04 | 1.64 |
|   | 185.4 | 8064.66162 | 186.89 | 1.49 | 0.80 |
|   | 185.4 | 7980.31494 | 184.90 | −0.50 | −0.27 |
|   | 185.4 | 7685.14844 | 177.96 | −7.44 | −4.01 |

Specificity

An important prerequisite for specificity is that the HA1 HPLC peak shows sufficient purity. The isolated peak of HA1 was checked by SDS-PAGE. Using SDS-PAGE with Coomassie staining, isolated HA1 migrates as a single band. This HA1 band was further analyzed by an in-gel digestion and LC-MS/MS analysis for identification of protein in the band. This band contained exclusively HA1. A more sensitive way to analyze proteins in the HA1 peak was to perform the digest directly on the collected fraction after lyophilization.

For all the identified peptides, the height of the peak in the reconstructed ion chromatogram was measured to estimate the purity of the contained proteins. As different peptides have different ionization efficacies, this method was used as an estimate of which proteins were detectable and an approximate relative quantification.

TABLE 12

Purity of isolated peak 1 and peak 2 from the HA1 double peak

| No. | Reference | P (pro)[1] | Score[2] | Sum Peak Height of all identified peptides | % Height |
|---|---|---|---|---|---|
| 1 | HA Influenza A virus (A/California/07/2009 (H1N1) | 1.09E−09 | 130.15 | 55264118 | 96.39 |
| 2 | Actin Host cell related | 1.17E−07 | 56.17 | 1226697 | 2.14 |
| 3 | Cofilin-1 Host cell related | 2.33E−11 | 50.20 | 477875 | 0.83 |
| 4 | Nucelocapsid protein Influenza A virus | 9.24E−07 | 20.14 | 365744 | 0.64 |
| Sum | | | | 57334434 | 100.00 |

[1]P (pro) is the probability for the protein match (the lower the value the better the match)
[2]is a parameter for the quality of the SEQUEST search (the higher the value the better the match)

As can be seen in Table 12, the HA1 peak contains >96% HA1. Minor impurities were identified as nucleoprotein and host cell proteins (actin and cofilin-1).

Precision

To show the precision of the method for determining HA content in sample 2, a total of 12 determinations of HA content were carried out on two days (6 on each day) at two concentrations, 23.175 ηg/ml and 92.7 μg/ml. Intra-day precision was 2.96% and 1.77% for the lower concentration and 0.81% and 0.89% for the higher concentration samples. Relative standard deviation (RSD) was 2.19% for the lower concentration sample and 1.30% for the higher concentration sample.

TABLE 13

HA quantification of sample 2 diluted 1:4 with deionized-water, precision at 23.175 μg/ml

| Repeat | Day 1 [μg/ml] | Day 2 [μg/ml] | All data [μg/ml] |
|---|---|---|---|
| 1 | 22.80 | 22.72 | |
| 2 | 22.42 | 23.41 | |
| 3 | 23.74 | 22.70 | |
| Mean | 22.99 | 22.94 | 22.97 |
| RSD | 2.96% | 1.77% | 2.19% |

TABLE 14

HA quantification of sample 2, precision at 92.7 μg/ml

| Repeat | Day 1 [μg/ml] | Day 2 [μg/ml] | All data [μg/ml] |
|---|---|---|---|
| 1 | 91.32 | 94.87 | |
| 2 | 92.44 | 93.73 | |
| 3 | 92.74 | 93.24 | |
| Mean | 92.17 | 93.95 | 93.06 |
| RSD | 0.81% | 0.89% | 1.30% |

The disclosure has been described in terms of particular embodiments found or proposed to comprise specific modes for the practice of the disclosure. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for isolating an antigen from a vaccine composition, the method comprising the steps of:
    (a) solubilizing the antigen in the vaccine composition by reduction without a detergent and without an alkylating agent, wherein the reduction comprises an incubation temperature of about 70° C., about 75° C., about 80° C., about 85° C., or about 90° C.; and
    (b) isolating the antigen or an antigen subtype by fractionation.

2. The method of claim 1, wherein the reduction comprises treating the vaccine composition with dithiothreitol.

3. The method of claim 1, wherein the solubilizing step further comprises denaturing with a chaotropic agent.

4. The method of claim 1, wherein the reduction is further carried out by acidification of the antigen or antigen subtype to prevent disulfide bond formation between separated antigen subtypes.

5. A method for quantifying antigen or antigen subtype in a vaccine composition, the method comprising the method of claim 1 with a further step of quantifying the antigen or antigen subtype.

6. The method of claim 5, wherein the quantifying step is carried out without using an antigen standard.

7. The method of claim 5, wherein the quantifying step is carried out using an antigen standard.

8. The method of claim 5, wherein the quantifying step comprises quantifying antigen by amino acid analysis.

9. The method claim 1, wherein the reduction comprises an incubation time from about 5 minutes to about 20 hours.

10. The method of claim 1, wherein the reduction comprises an incubation time from about 30 minutes to about 2 hours.

11. The method of claim 1, wherein the reduction comprises an incubation time of about 1 hour.

12. The method of claim 1, wherein the reduction comprises an incubation temperature at about 85° C.

13. The method of claim 3, wherein the chaotropic agent is guanidine hydrochloride, urea, thiourea, lithium, perchlorate, or thiocyanate.

14. The method of claim 4, wherein the acidification is carried out with phosphoric acid, hydrochloric acid, sulfuric acid, trifluoroacetic acid, pentafluoropropionic acid, heptafluorobutyric acid, or formic acid.

15. The method of claim 1, wherein fractionation is carried out by chromatography.

16. The method of claim 15, wherein the chromatography is high performance liquid chromatography (HPLC), reversed-phase HPLC (RP-HPLC), ion exchange-HPLC (IEX-HPLC), affinity chromatography, hydrophobic interaction chromatography (HIC), or size exclusion chromatography (SEC).

17. The method of claim 16, wherein the chromatography is RP-HPLC.

18. The method of claim 1, wherein the antigen is viral or bacterial.

19. The method of claim 1, wherein the antigen is hemagglutinin (HA).

20. The method of claim 19, wherein the HA is from an Influenza virus vaccine composition, a measles virus vaccine composition, a parainfluenza virus vaccine composition, or a mumps virus vaccine composition.

21. The method of claim 1, wherein the vaccine composition is an Influenza virus vaccine composition.

22. The method claim 21, wherein the Influenza virus vaccine composition provides protection from an Influenza virus selected from the group consisting of Influenza A and Influenza B.

23. The method of claim 1, wherein the antigen subtype is any one of Influenza A HA1, HA2, HA3, HA4, HA5, HA6, HA7, HA8, HA9, HA10, HA11, HA12, HA13, HA14, HA15, and HA16 or Influenza B HA.

24. The method of claim 23, wherein the antigen subtype is any one of Influenza A HAL HA2, HA3, HA5, HA7, HA9, HA10, or Influenza B HA.

25. The method of claim 24, wherein the Influenza A HA subtype is HA1.

26. The method of claim 21, wherein the Influenza vaccine composition provides protection from an Influenza type selected from the group consisting of Influenza A H1N1, H1N2, H2N2, H3N2, H5N1, H7N1, H7N2, H7N3, H7N7, H9N2, H10N7, and Influenza B.

27. The method of claim 5, wherein the method quantifies antigen content with a relative standard deviation (RSD) of less than about 2.5%.

28. The method of claim 27, wherein the RSD is about 2.2%.

29. The method of claim 27, wherein the RSD is about 1.3%.

* * * * *